(12) United States Patent
Frederick et al.

(10) Patent No.: US 11,278,743 B1
(45) Date of Patent: Mar. 22, 2022

(54) SELECTING IMAGING PERSPECTIVES TO OPTIMIZE TRACKING VOLUME DETECTABILITY AND MODEL QUALITY

(71) Applicant: ACCURAY INCORPORATED, Sunnyvale, CA (US)

(72) Inventors: Charles Brandon Frederick, Sunnyvale, CA (US); Robert Elijah Broadhurst, Carrboro, NC (US); Eric Schnarr, McFarland, WI (US)

(73) Assignee: Accuray Incorporated, Sunnyvale, CA (US)

( * ) Notice: Subject to any disclaimer, the term of this patent is extended or adjusted under 35 U.S.C. 154(b) by 4 days.

(21) Appl. No.: 17/014,021

(22) Filed: Sep. 8, 2020

(51) Int. Cl.
*A61N 5/00* (2006.01)
*A61N 5/10* (2006.01)
*G06K 9/32* (2006.01)

(52) U.S. Cl.
CPC ........... *A61N 5/1049* (2013.01); *A61N 5/107* (2013.01); *G06K 9/3233* (2013.01); *A61N 2005/1055* (2013.01)

(58) Field of Classification Search
CPC .................. A61N 5/1049; A61N 5/107; A61N 2005/1055; G06K 9/3233; A61B 6/00; A61B 6/06; A61B 6/10; A61B 6/4417; A61B 6/54; A61B 6/545; A61B 6/547
See application file for complete search history.

(56) References Cited

U.S. PATENT DOCUMENTS 10,342,996 B2 * 7/2019 Jordan ................. A61N 5/1081

* cited by examiner

*Primary Examiner* — Jurie Yun
(74) *Attorney, Agent, or Firm* — Womble Bond Dickinson (US) LLP (57) ABSTRACT

An image of a region of interest (ROI) is identified from a first perspective, the image having an uncertainty value associated with the ROI. A model is generated comprising one or more parameters associated with the ROI based on the image. A plurality of tracking quality metrics for a plurality of perspectives that a subsequent image may be captured from by an imaging system of the ROI are determined using the model, the tracking quality metrics indicating a reduction of the uncertainty value associated with the ROI by the subsequent image. A second perspective of the plurality of perspectives for the subsequent image is selected based on a corresponding tracking quality metric of the plurality of tracking quality metrics for the second perspective indicating a reduction of the uncertainty value.

24 Claims, 8 Drawing Sheets

SELECTING IMAGING PERSPECTIVES TO OPTIMIZE TRACKING VOLUME DETECTABILITY AND MODEL QUALITY

TECHNICAL FIELD

The present disclosure relates to selecting imaging perspectives to optimize tracking volume detectability and model quality.

BACKGROUND

In radiation treatment, a radiation delivery system may utilize motion tracking to determine a correlation between a motion of an intended target or region of interest and a direct measurement of a position of a tracking structure. The correlation is determined by fitting a motion model that registers the target or region of interest and predicts the motion relative to the tracking structure.

BRIEF DESCRIPTION OF THE DRAWINGS

The present disclosure will be understood more fully from the detailed description given below and from the accompanying drawings of various implementations of the disclosure.

DETAILED DESCRIPTION

Described herein are embodiments of methods and apparatus for selecting imaging perspectives to optimize tracking volume detectability and model quality. A radiation delivery system may utilize high-frequency online motion tracking. The high-frequency online motion tracking depends upon a correlation between the motion of an intended target and a low-frequency but accurate and direct measurement (for example, a two-dimensional (2D) x-ray image) of the position of a tracking structure (assumed to be moving in tandem with the target) and a high frequency motion surrogate (for example, an LED marker tracking respiratory or other quasi-periodic motion or nothing under a static target assumption).

To acquire the low-frequency direct measurements, the radiation delivery system may include an imaging system, such as a kilovolt (kV) or magnetic resonance (MR) imaging system, to capture 2D x-ray images of a region of interest (ROI) that may include the tracking structure.

When acquiring these images, there is a tradeoff between the amount of non-therapeutic imaging dose (and/or imaging time/frequency) and position uncertainty. For example, taking a smaller number of images reduces the non-therapeutic imaging dose that a patient is exposed to, but increases the position uncertainty (also referred to as "under-sampling" hereafter). Conversely, taking a larger number of images reduces the position uncertainty, but increases the non-therapeutic imaging dose that the patient is exposed to (also referred to as "over-sampling" hereafter). Accordingly, it is important to balance both of these considerations when determining what times these images are to be captured at and/or what perspectives these images are to be captured from.

Aspects of the disclosure may remedy the above and other deficiencies by selecting imaging perspectives and/or times that optimize tracking volume and model quality. When an image of an ROI is acquired from a first perspective, the image may have an uncertainty value that corresponds to a position uncertainty associated with the ROI. For example, the uncertainty value may correspond to a position uncertainty of a tracking structure or a target within the ROI.

Processing logic of a processing device may generate a model associated with the ROI based on the image. The model may include on or more parameters associated with the ROI. In embodiments, the one or more parameters may be any characteristics or values that may influence the position uncertainty of the ROI. Examples of parameters associated with the ROI may include, but are not limited to, a respiratory motion trajectory associated with the ROI, radiation sensitive structures within the ROI, visibility of the ROI, or a perspective of the ROI.

The processing logic may use the model to determine tracking quality metrics for multiple perspectives that a subsequent image may be captured from of the ROI. The tracking quality metrics may indicate a reduction of the uncertainty value associated with the ROI by a subsequent image that would be captured from each of the perspectives. The tracking quality metrics may be used to identify one or more perspectives that have high reductions of the uncertainty value relative to other perspectives.

The processing logic may select a second perspective from the multiple perspectives for the capturing of a subsequent image based on the tracking quality metrics. The processing logic may select the second perspective based on a corresponding tracking quality metric indicating that the subsequent image from the second perspective would reduce the uncertainty value associated with the ROI. Selecting the second perspective ensures that the subsequent image will decrease the position uncertainty of the ROI, preventing the capturing of subsequent images that may not contain useful information (e.g., do not improve position uncertainty of the ROI) and reducing or eliminating over-sampling. By reducing or eliminating over-sampling, the non-therapeutic imaging dose that a patient may be exposed to is also reduced, improving the performance of the radiation delivery system.

Although embodiments of the disclosure are described in the context of a radiation delivery system, such descriptions are provided for illustrative purposes only. Aspects of the disclosure may be utilized by any type of imaging system that would benefit from the optimization of selection of imaging perspectives of a ROI. For example, aspects of the disclosure may be utilized by various types of surgical guidance systems that include imaging systems. Furthermore, although embodiments of the disclosure may be described utilizing a kV imaging system, aspects of the disclosure may be utilized by other types of imaging systems, such as MR imaging systems or megavolt (MV) imaging systems.

In embodiments, aspects of the disclosure may provide for an improved MR imaging system. Because MR imaging does not involve a radiation dose, reducing a patient's exposure to radiation is not required when utilizing an MR imaging system. However, aspects of the disclosure may be used to optimize the position, orientation, and/or timing of images that are acquired of an ROI using an MR imaging system. For example, MR imaging systems may be unable to capture a three-dimensional (3D) image quickly enough to capture motion across an entire ROI. Rather than attempting to capture a 3D image of the ROI, multiple one-dimensional (1D) or 2D MR images (which can be acquired more quickly than a 3D image) may be acquired from a variety of positions and orientations within the ROI. Aspects of the disclosure may be utilized to optimize the position, orientation, and/or timing of these images to minimize the uncertainty associated with tracking key targets and sensitive structures within the ROI using an MR imaging system.

Figure 1A:
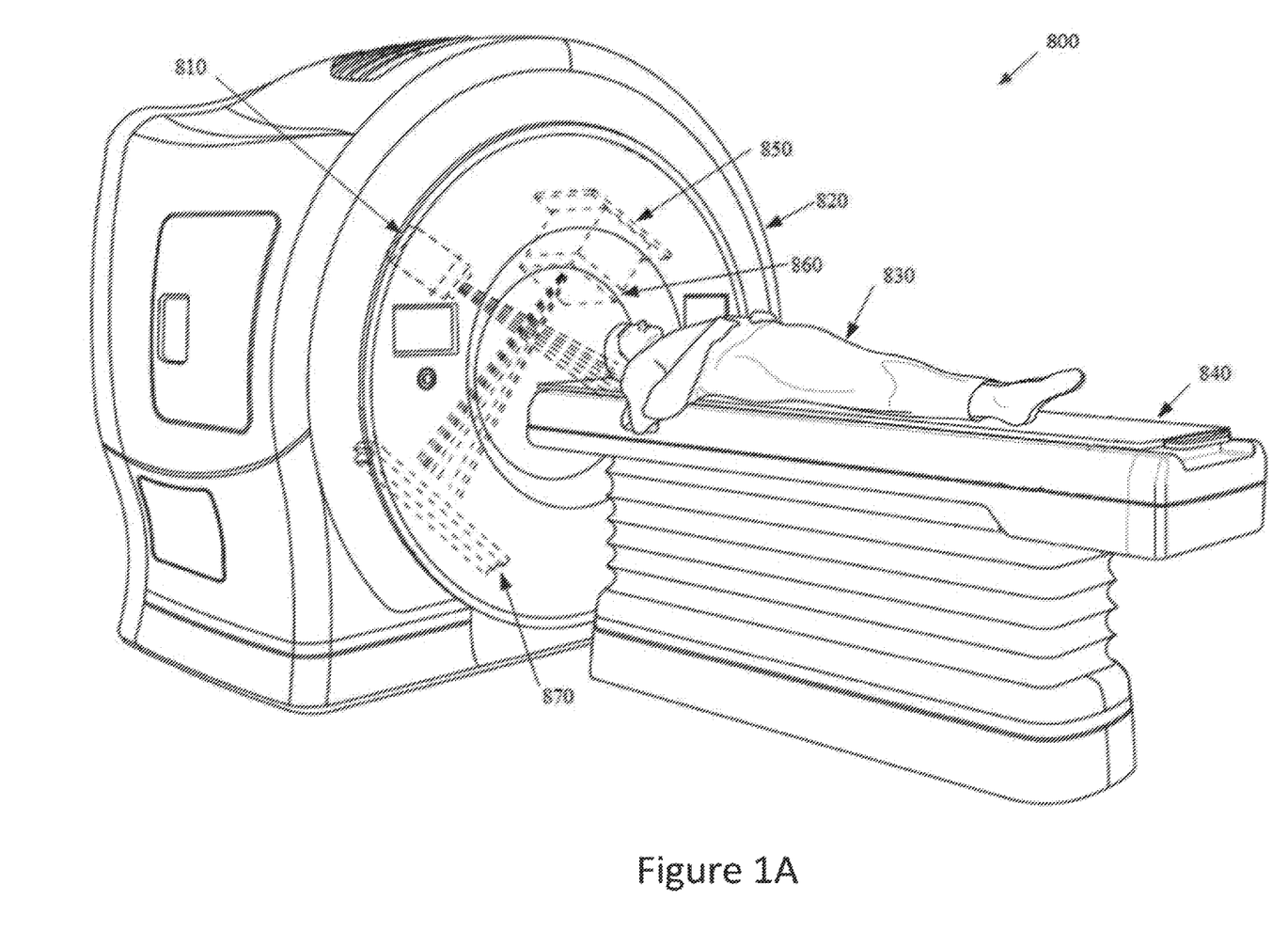
FIG. 1A illustrates a helical radiation delivery system, in accordance with embodiments described herein.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multileaf collimator (MLC) 860 coupled with the distal end of the LINAC 850. The MLC includes a housing that houses multiple leaves that are movable to adjust an aperture of the MLC to enable shaping of the treatment beam. In embodiments, the MLC 860 may be a binary MLC that includes a plurality of leaves arranged in two opposing banks, where the leaves of the two opposing banks are interdigitated with one another and can be opened or closed to form an aperture. In some embodiments, the MLC 860 may be an electromagnetically-actuated MLC. In embodiments, MLC 860 may be any other type of MLC. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

The helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In one embodiment, the helical radiation delivery system 800 may also include a secondary imaging system consisting of a kV imaging source 810 mounted orthogonally relative to the LINAC 850 (e.g., separated by 90 degrees) on the ring gantry 820 and may be aligned to project an imaging x-ray beam at a target region and to illuminate an imaging plane of a detector after passing through the patient 130.

Figure 1B:
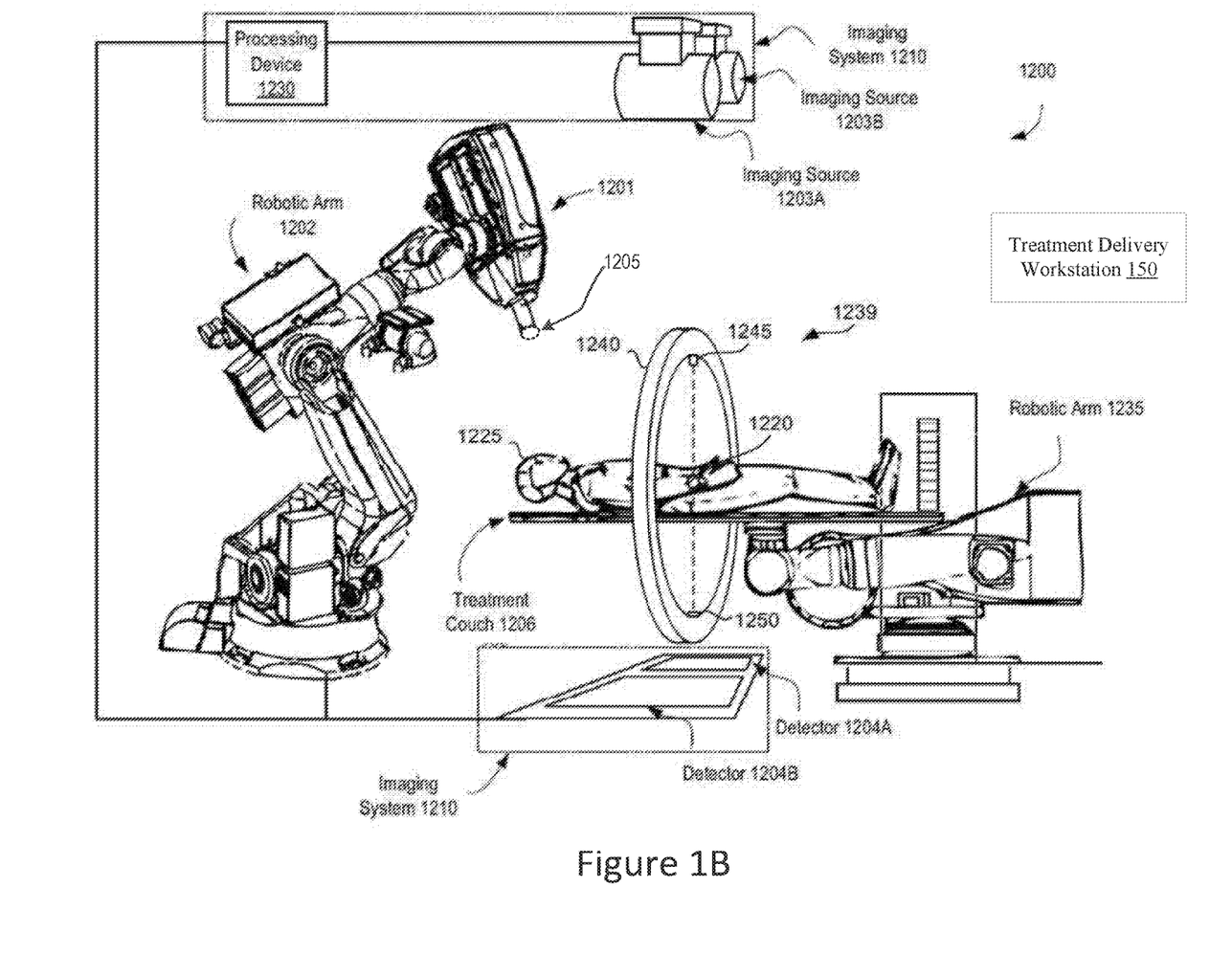
FIG. 1B illustrates a robotic radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 coupled with the distal end of the LINAC 1201 to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

In another embodiment, the robotic arm 1202 and LINAC 1201 at its end may be in continuous motion between nodes while radiation is being delivered. The radiation beam shape and 2-D intensity map is determined by rapid motion of the leaves in the MLC 1205 during the continuous motion of the LINAC 1201.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 1203A, 1203B and/or x-ray detectors 1204A, 1204B may be mobile, in which case they may be repositioned to maintain alignment with the target, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

In one embodiment, IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1B, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

Figure 1C:
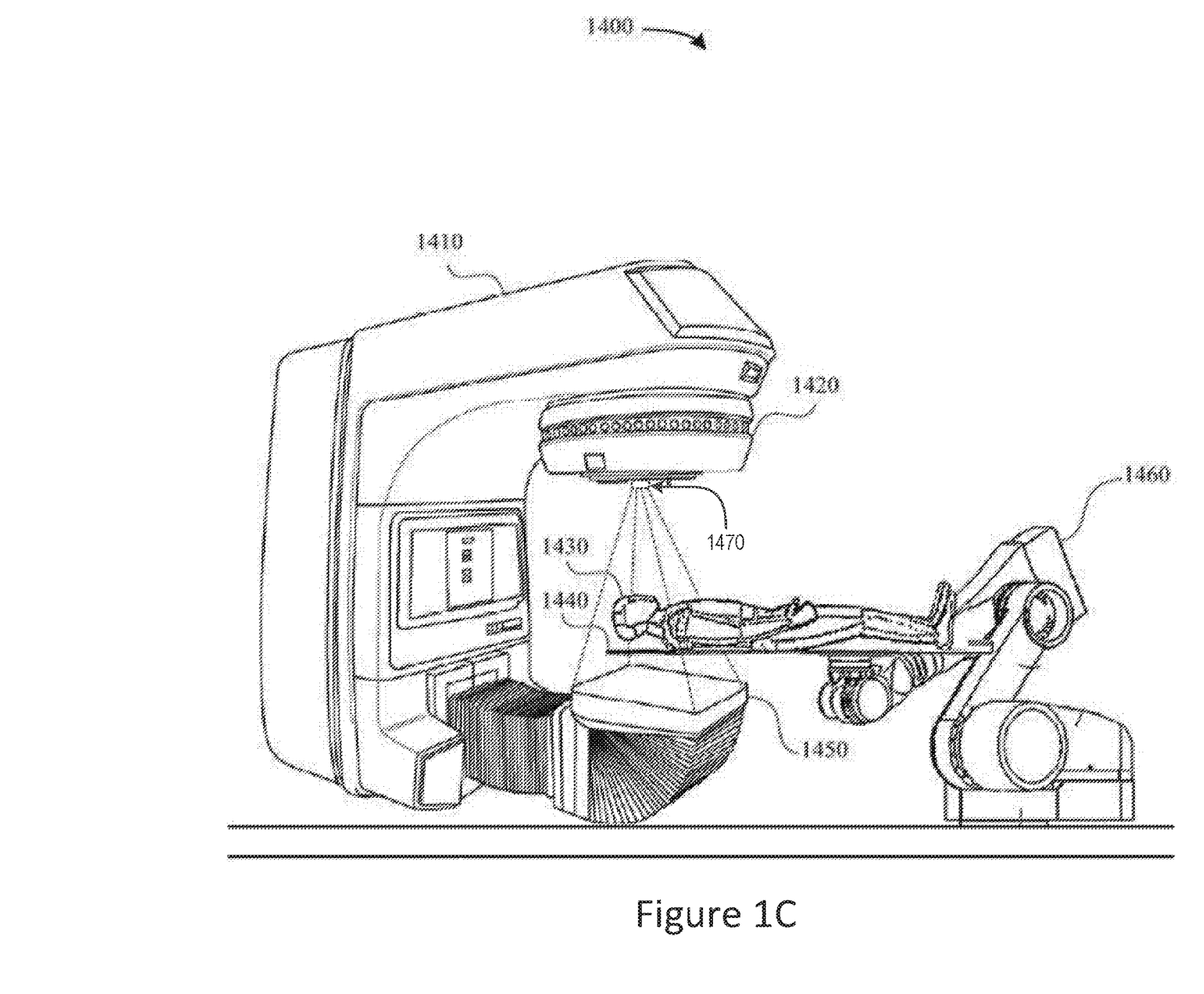
FIG. 1C illustrates a C-arm gantry-based radiation treatment system, in accordance with embodiments described herein.

FIG. 1C illustrates a C-arm radiation delivery system 1400. In one embodiment, in the C-arm system 1400 the beam energy of a LINAC may be adjusted during treatment and may allow the LINAC to be used for both x-ray imaging and radiation treatment. In another embodiment, the system 1400 may include an onboard kV imaging system to generate x-ray images and a separate LINAC to generate the higher energy therapeutic radiation beams. The system 1400 includes a C-arm gantry 1410, a LINAC 1420, an MLC 1470 coupled with the distal end of the LINAC 1420 to shape the beam, and a portal imaging detector 1450. The C-arm gantry 1410 may be rotated to an angle corresponding to a selected projection and used to acquire an x-ray image of a VOI of a patient 1430 on a treatment couch 1440. In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 2:
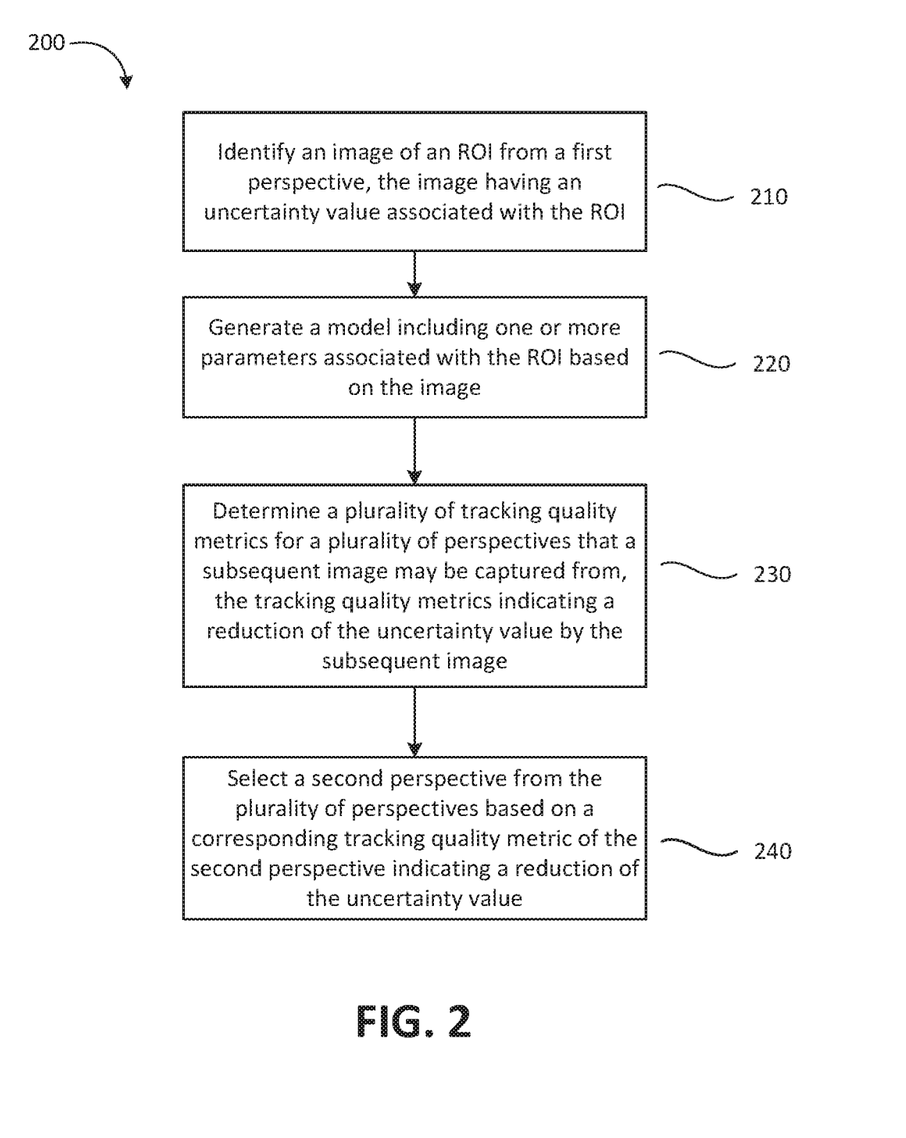
FIG. 2 depicts a flow diagram of a method of selecting imaging perspectives to optimize tracking volume detectability and model quality, in accordance with embodiments of the disclosure.

FIG. 2 depicts a flow diagram of a method 200 of selecting imaging perspectives to optimize tracking volume detectability and model quality, in accordance with embodiments of the disclosure. Method 200 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In embodiments, various portions of method 200 may be performed by processing logic of a processing device of a radiation delivery system as previously described at FIGS. 1A-1C.

With reference to FIG. 2, method 200 illustrates example functions used by various embodiments. Although specific function blocks ("blocks") are disclosed in method 200, such blocks are examples. That is, embodiments are well suited to performing various other blocks or variations of the blocks recited in method 200. It is appreciated that the blocks in method 200 may be performed in an order different than presented, and that not all of the blocks in method 200 may be performed.

Method 200 begins at block 210, where the processing logic identifies an image of an ROI from a first perspective that has an uncertainty value associated with the ROI. In embodiments, the uncertainty value may correspond to a position uncertainty associated with the ROI and/or one or more objects within the ROI. For example, the uncertainty value may correspond to a position uncertainty associated with tracking structure within the ROI.

In some embodiments, the image of the ROI may be acquired by an imaging system during a treatment session being administered by a radiation delivery system. In embodiments, the image of the ROI may be a previously acquired image. For example, the image may be an image of the ROI that was previously captured as part of a treatment planning session.

At block 220, the processing logic generates a model that includes one or more parameters associated with the ROI based on the image. The one or more parameters may be any characteristics or values that may influence the position uncertainty of the ROI. In embodiments, the parameters may include a respiratory motion trajectory of a patient associated with the ROI. The respiratory motion trajectory may describe the motion of the ROI during different phases of the patient's respiratory cycle and include the timing of the various phases of the respiratory cycle. In embodiments, the parameters may include radiation sensitive structures within the ROI or in proximity to the ROI. For example, the parameters may indicate the rectum of a patient is within the ROI or is in proximity to the ROI. In an embodiment, the parameters may include a visibility of the ROI by the imaging system. In embodiments, the parameters may include a perspective of the ROI. In some embodiments, other parameters may be used in the model.

At block 230, the processing logic determines tracking quality metrics for perspectives that a subsequent image may be captured from. The tracking quality metrics may indicate whether a subsequent image captured from each of the perspectives will reduce the uncertainty value of the image identified at block 210. In embodiments, the tracking quality metrics may be determined by examining higher order terms of a Taylor Series of a model fitting objective function, L, as is shown below:

$$\hat{L} = \sum_t d_t(p_t, \mathcal{P}_t(f_s(m_t)))$$

$$\hat{s} = \arg\min_s \hat{L}$$

where:

t is the time at when the measurements are made. For a rotating gantry, this time may also specify imaging system and patient support positions with respect to a treatment beam.

$p_t$ are a set of tracking structure measurements or detected or candidate positions of the tracking structure in a 2D x-ray image $m_t$ is the high-frequency surrogate motion data $f_s$ is the motion model that converts high-frequency data to the position of the tracking structure s are the parameters of the motion model $P_t$ is the projection operator that relates the 3D data to its corresponding 2D data in the x-ray image. For the case of points, this is a perspective projection matrix. For image data, this is a DRR generator.

d is some distance function that weights the similarity between the 2D measured data $p_t$ and the tracking structure in its 2D predicted location according to the model. In embodiments, the distance function may reflect the magnification of the error due to the 3D location of the tracking structure with respect to the imaging geometry. In some embodiments, the distance function may reflect a priori uncertainties in the measurements. In an embodiment, the distance function may reflect age related down-weighting of older measurements. In embodiments, the distance function may reflect spatial probability distribution of the candidate tracking structure to image match, weighting the error vector based on the quality of the 2D image data. In some embodiments, the distance function may reflect other factors reflecting the statistical quality of the model as an estimate of its ability to describe the motion of the tracking structure.

The value of the model fitting objective function may be used to evaluate the model quality for the ROI, where a smaller value of the objective function $\hat{L}$ indicates a better model fit for the ROI. However, this may not necessarily describe the quality of the model in predicting a motion associated with the ROI. For example, this may not describe how the model predicts respiratory motion of a patient associated with the ROI.

An additional measure of the quality of the model fitting may be found by examining the shape of $\hat{L}$ with respect to s at the minimum, where the optimal model parameters $\hat{s}$ have already been found. Consider the Taylor series expansion of $\hat{L}$ about $\hat{s}$:

$$\hat{L}(s) \approx \hat{L}(\hat{s}) + \nabla \hat{L}(\hat{s})(s-\hat{s}) + \frac{1}{2}(s-\hat{s})^T \nabla^2 \hat{L}(\hat{s})(s-\hat{s}) + \ldots$$

where the first term is the value of the objective function at the minimum, the second term is a gradient of the objective function, and the third term is the Hessian matrix—the matrix of second derivatives of the objective function:

$$\nabla^2 \hat{L}(\hat{s}) = H\hat{L}(\hat{s}) = \frac{\partial^2 \hat{L}(\hat{s})}{\partial s_i \partial s_j}$$

with Hessian operator H taken with respect to the parameters of the model. This matrix may describe the curvature of the function. A large curvature means that, given a small step in a direction s' in model parameter space, the value of the function changes a large amount. If, the curvature is very large in a particular direction, there is greater certainty about the location of the minimum in that direction because the function/measurements are more sensitive to changes in parameters in that direction.

When Hessians are at a minima of s' the Hessian may be a symmetric, positive-definite (SPD) matrix. Such a matrix can be thought of as describing an ellipsoid (centered at zero) or quadratic field where iso-likelihood objective function values are ellipsoidal. SPD matrices are the form of covariance matrices, and the Hessian matrix at a minimum can be thought of as describing the covariance of the (normal) distribution from which model parameters are drawn as follows:

$$N\left(\hat{s}, \sum_s\right) \propto e^{-\frac{1}{2}(s-\hat{s})^T H\hat{L}(\hat{s})(s-\hat{s})} \Rightarrow e^{-\frac{1}{2}(s-\hat{s})^T \Sigma_s^{-1}(s-\hat{s})}$$

The above equation described a distribution of parameters of the generated model. The covariance of the distribution, $\Sigma_s$, is the inverse of the Hessian, where the Hessian curvature matrix can be thought of as a certainty matrix and its inverse as an uncertainty matrix, where a small uncertainty may be desirable. A model quality may be greater if the variance of the distribution from which the model's parameters are drawn is smaller (e.g., corresponding to a Hessian matrix that is large). Thus, the optimal next imaging time is the time at which that image is capable of maximally increasing the largeness of the Hessian of the objective function. Alternatively (or in addition), the next optimal imaging time could also enforce that a minimum amount of expected error (given by uncertainty) is maintained.

To determine an optimal perspective for capturing an image, another angle may be added to the image set:

$$\hat{L}' = \sum_t d_t(p_t, \mathcal{P}_t(f_s(m_t))) + d_{t'}(p_{t'}, \mathcal{P}_{t'}(f_s(a_{t'})))$$

where t' corresponds to a time in the future when the new tracking measurement is to be acquired and $a_{t'}$ corresponds to the predicted value of the high-frequency motion surrogate at time t'. The Hessian may be computed with respect to the model parameters to determine the certainty after the subsequent image:

$$H\hat{L}' = H\hat{L} + Hd_{t'}(p_{t'}, \mathcal{P}_{t'}(f_s(a_{t'})))$$

The determinant may be considered as a measure of the largeness of the certainty matrix. The determinant of an SPD is proportional to the volume of the ellipsoid that it represents. Therefore, the optimal imaging time may be:

$$\arg\max_{t'} det[H\hat{L} + Hd_{t'}(p_{t'}, \mathcal{P}_{t'}(f_s(a_{t'})))]$$

Reasonable extrapolation may be used to predict the unknown values at time, t'. The problem is tractable because it is a one-dimensional optimization over a discrete set of imaging perspectives/times. In embodiments, this problem may be made more general by solving for multiple, future time points, For example, higher quality time points may be estimated if points for a full gantry rotation are estimated at once, taking into account any temporal limitations for the set of points.

Each of the terms in the determinant may be an SPD matrix that defines an ellipsoid. The sums of the SPD matrices are SPD, resulting in the sums also representing an ellipse. The optimal time/perspective for a subsequent image may correspond to the time/perspective that produces a certainty ellipsoid that, when added to the first ellipsoid, produces an ellipsoid that is the largest.

At block 240, the processing logic selects a second perspective from the multiple perspectives based on a corresponding tracking quality metric of the second perspective indicating a reduction of the uncertainty value. In embodiments, the processing logic may select the second perspective based on the corresponding tracking quality metric indicating a greatest reduction of the uncertainty value of the multiple perspectives. In an embodiment, the processing logic may select the second perspective based on the corresponding tracking quality metric indicating a reduction of uncertainty value that exceeds a threshold. In some embodiments, the processing logic may select the second perspective based on other criteria. In embodiments, the processing logic may select the second perspective automatically (e.g., without user intervention) during a treatment session of a radiation delivery system.

Figure 3A:
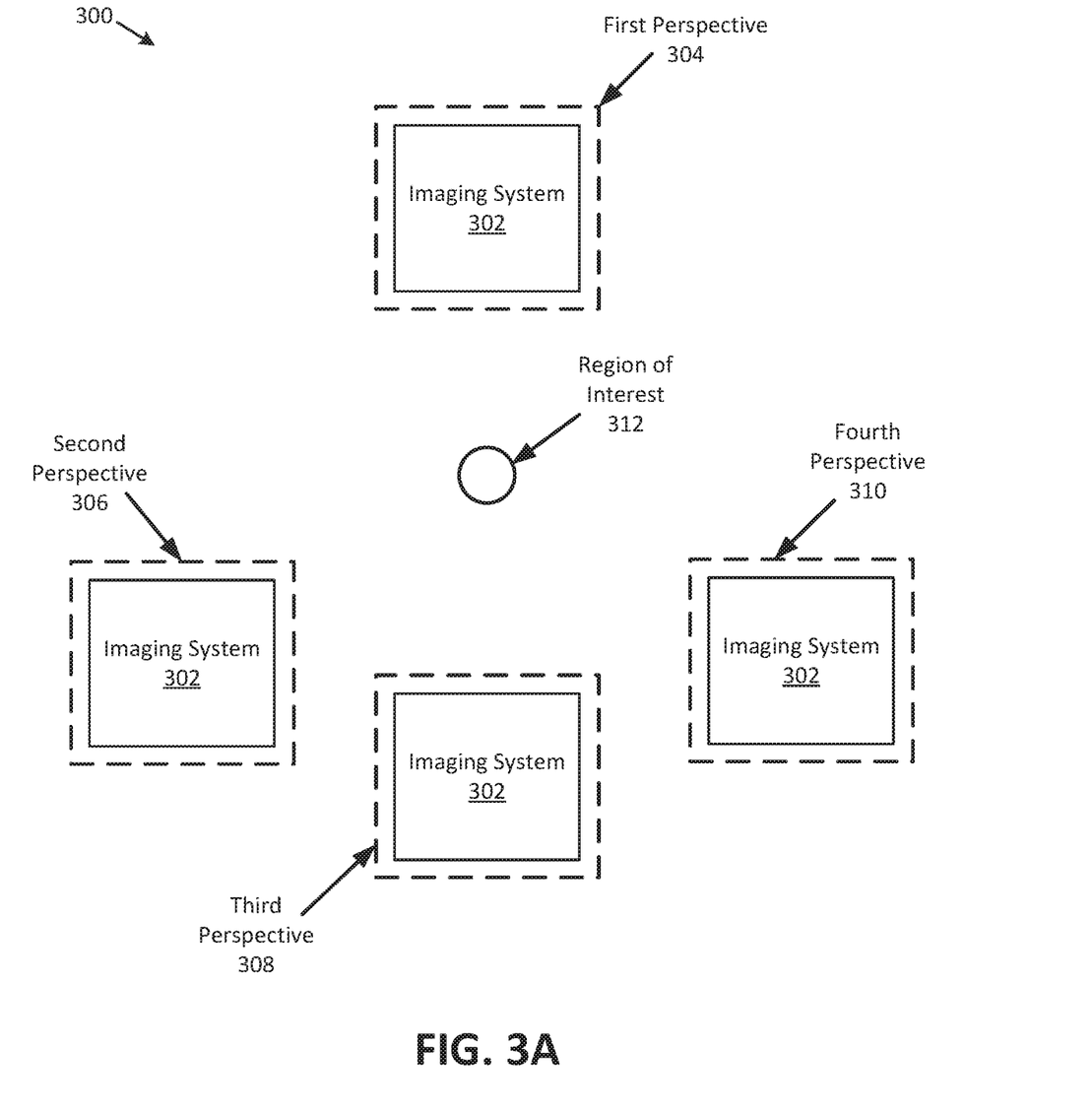
FIG. 3A is an illustration of an example of an imaging system having multiple perspectives of a region of interest, in accordance with embodiments of the disclosure.

FIG. 3A is an illustration 300 of an example of an imaging system having multiple perspectives of a region of interest, in accordance with embodiments of the disclosure. Illustration 300 includes imaging system 302 that may be an X-ray (kV or MV) imaging system, an MR imaging system, or any other type of imaging system. In embodiments, the imaging system 302 may correspond to kV imaging source 810 of FIG. 1A or imaging system 1210 of FIG. 1B. In some embodiments, the imaging system 302 may include an imaging detector (not shown), as previously described at FIGS. 1A-C.

In embodiments, the imaging system 302 may be coupled to a ring gantry, such as ring gantry 820 of FIG. 1A. In an embodiment, the imaging system 302 may be coupled to a robotic arm, such as robotic arm 1202 of FIG. 1B. In some embodiments, the imaging system 302 may be coupled to a C-arm gantry, such as C-arm gantry 1410 of FIG. 1C.

Illustration 300 further includes a region of interest 312. In embodiments, the region of interest 312 may correspond to a region of interest of a patient. The region of interest 312 may include one or more targets and/or tracking structures.

Illustration 300 includes first perspective 304, second perspective 306, third perspective 308, and fourth perspective 310 that may correspond to different perspectives from which an image of the region of interest 312 may be captured. In embodiments, the first perspective 304 may correspond to the perspective from which a first image was captured, as described at block 210 of FIG. 2. In some embodiments, the second perspective 306, third perspective 308, and fourth perspective 310 may correspond to a subset of the multiple perspectives considered to capturing a subsequent image of the region of interest 312, as described at blocks 230 and 240 of FIG. 2.

In embodiments where imaging system 302 is coupled to a gantry, first perspective 304, second perspective 306, third perspective 308, and fourth perspective 310 may correspond to different angles as the imaging system 302 relative to the region of interest 312 as the imaging system 302 is rotated about the region of interest 312 by the gantry. In embodiments where imaging system is coupled to a robotic arm, first perspective 304, second perspective 306, this perspective 308, and fourth perspective 310 may correspond to different orientations relative to the region of interest 312 as the imaging system 302 is positioned along a path about the region of interest 312 by the robotic arm.

Figure 3B:
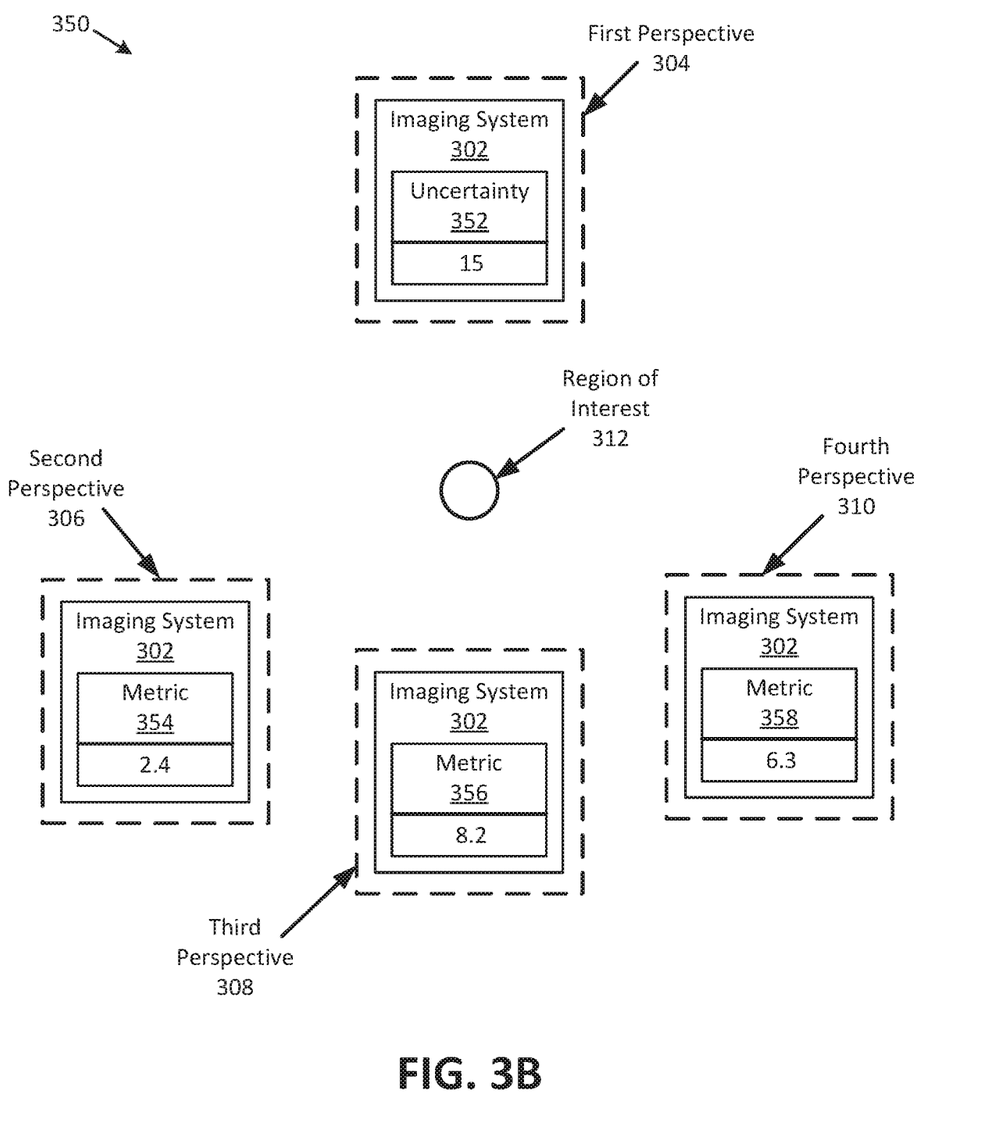
FIG. 3B is an illustration of an example of selecting a perspective for capturing a subsequent image based on tracking quality metrics, in accordance with embodiments of the disclosure.

FIG. 3B is an illustration 350 of an example of selecting a perspective for capturing a subsequent image based on tracking quality metrics, in accordance with embodiments of the disclosure. In illustration 350, the first perspective 304 corresponds to the perspective from which a first image has been captured. As previously described, the image may have an associated uncertainty value (e.g., uncertainty 352).

Second perspective 306, third perspective 308, and fourth perspective 310 may each have corresponding tracking quality metrics, metric 354, metric 356, and metric 358, respectively. As previously described, the tracking quality metrics may indicate a reduction in the uncertainty 352 value of the image captured from the first perspective 304. Upon determining metric 354, metric 356, and metric 358, processing logic of a processing device may select one of the second perspective 306, the third perspective 308, or the fourth perspective 310 for capturing a subsequent image of the region of interest 312.

Referring to FIG. 3B, metric 354 has a value of 2.4, metric 356 has a value of 8.2, and metric 358 has a value of 6.3. Because metric 356 has the largest value, metric 356 indicates that a subsequent image captured from the third perspective 308 may have a greatest reduction in the uncertainty 352 value of the first image relative to the second perspective 306 and the fourth perspective 310, which have lower corresponding metrics (e.g., metric 354 and metric 358). Accordingly, the processing logic may select the third perspective 308 for capturing a subsequent image.

In embodiments, a time may be selected by the processing logic for the capturing of the subsequent image from the third perspective 308. For example, if the region of interest 312 is a location that may be affected by the respiratory motion of a patient, the particular time for capturing the subsequent image from the third perspective may coincide with a particular respiratory phase of the patient to maximize the reduction in position uncertainty.

Although FIGS. 3A and 3B illustrate four perspectives for capturing a subsequent image, embodiments of the disclosure may include any number of perspectives that may be considered for the capturing of the subsequent image. Furthermore, although FIG. 3B described selecting the third perspective 308 based on a greatest reduction in uncertainty, embodiments of the disclosure may utilize other criteria for selecting a perspective for capturing the subsequent image.

Figure 4:
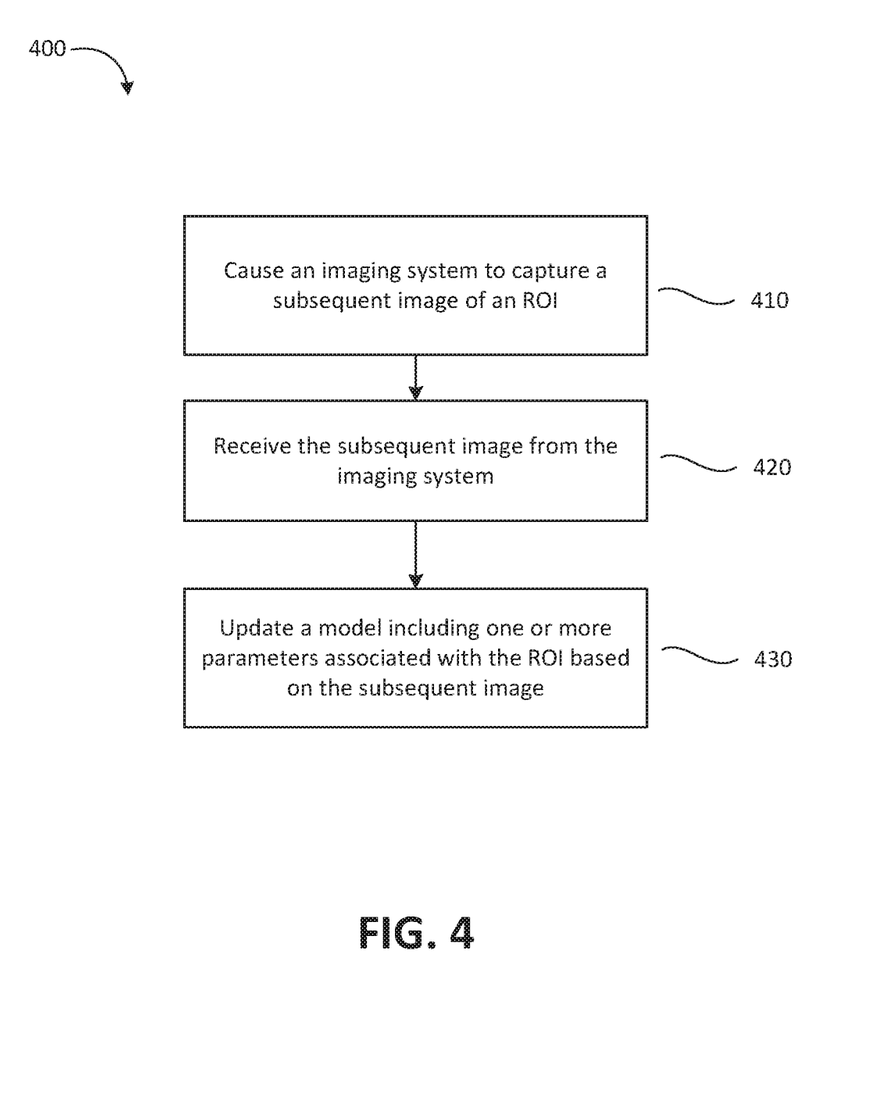
FIG. 4 depicts a flow diagram of a method of updating a model based on receiving a subsequent image of a region of interest, in accordance with embodiments of the disclosure.

FIG. 4 depicts a flow diagram of a method 400 of updating a model based on receiving a subsequent image of a region of interest, in accordance with embodiments of the disclosure. Method 400 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In embodiments, various portions of method 400 may be performed by processing logic of a processing device of a radiation delivery system as previously described at FIGS. 1A-1C.

With reference to FIG. 4, method 400 illustrates example functions used by various embodiments. Although specific function blocks ("blocks") are disclosed in method 400, such blocks are examples. That is, embodiments are well suited to performing various other blocks or variations of the blocks recited in method 400. It is appreciated that the blocks in method 400 may be performed in an order different than presented, and that not all of the blocks in method 400 may be performed.

Method 400 begins at block 410, where the processing logic causes an imaging system to capture a subsequent image of an ROI. The subsequent image may be captured from a perspective that is selected based on a reduction of an uncertainty value associated with a first image, as previously described at FIG. 2. In embodiments, the subsequent image may be captured during a treatment session being performed by a radiation delivery system.

At block 420, the processing logic receives the subsequent image from the imaging system.

At block 430, the processing logic updates a model including one or more parameters associated with the ROI based on the subsequent image. In embodiments, the model may correspond to the model generated at block 220 of FIG. 2. In some embodiments, updating the model may include modifying, adding, and/or removing parameters of the model. For example, upon receiving the subsequent image that includes additional information associated with a position of a radiation sensitive structure within the ROI, the processing logic may modify the parameter of the model that corresponds to the position of the radiation sensitive structure within the ROI.

Figure 5:
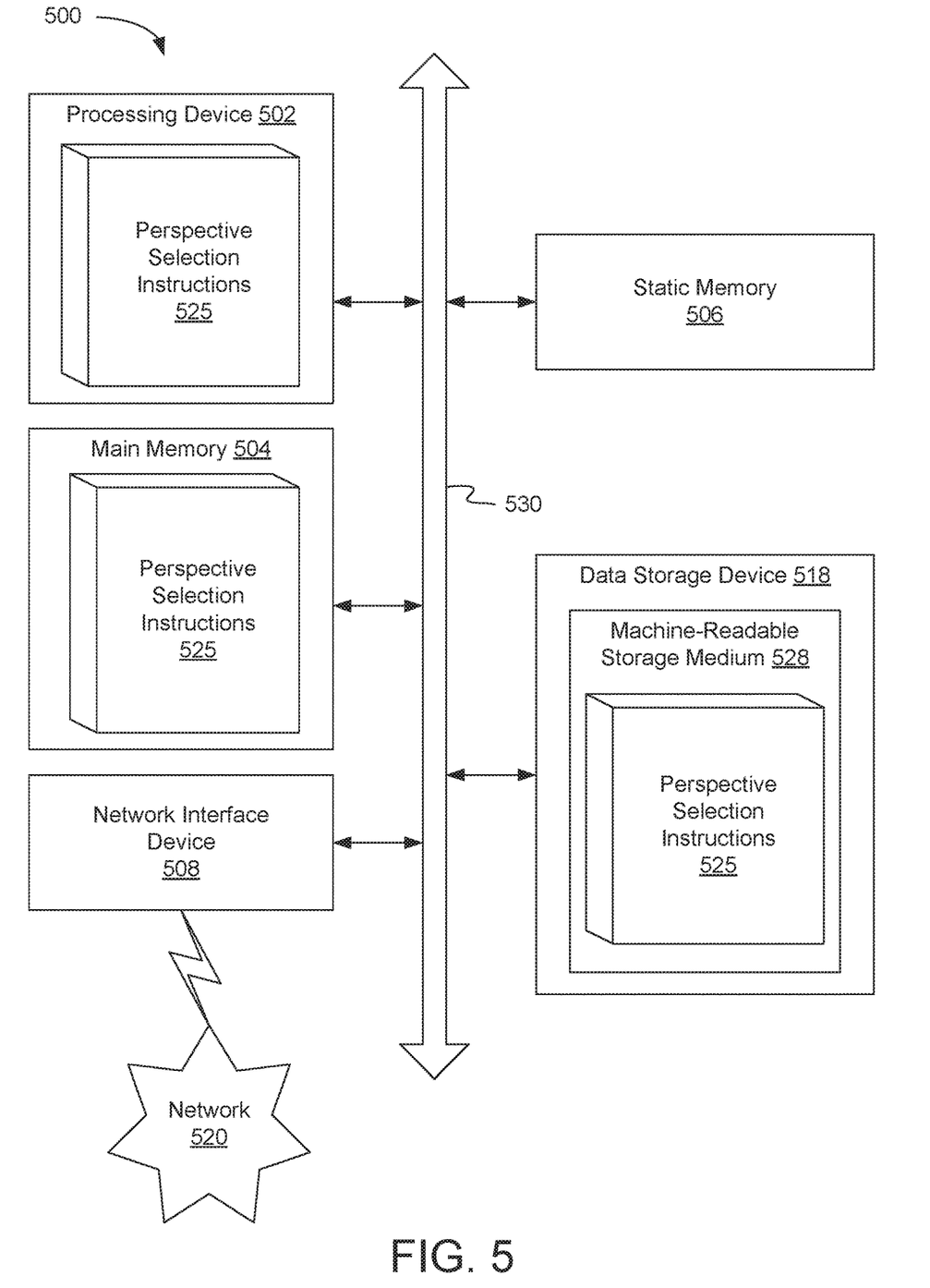
FIG. 5 is a block diagram of an example computing device that may perform one or more of the operations described herein, in accordance with some embodiments.

FIG. 5 is a block diagram of an example computing device 500 that may perform one or more of the operations described herein, in accordance with some embodiments. Computing device 500 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 500 may include a processing device (e.g., a general purpose processor, a PLD, etc.) 502, a main memory 504 (e.g., synchronous dynamic random access memory (DRAM), read-only memory (ROM)), a static memory 506 (e.g., flash memory and a data storage device 518), which may communicate with each other via a bus 530.

Processing device 502 may be provided by one or more general-purpose processing devices such as a microprocessor, central processing unit, or the like. In an illustrative example, processing device 502 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 502 may also comprise one or more special-purpose processing devices such as an application specific integrated circuit (ASIC), a field programmable gate array (FPGA), a digital signal processor (DSP), network processor, or the like. The processing device 502 may be configured to execute the operations described herein, in accordance with one or more aspects of the present disclosure, for performing the operations and steps discussed herein.

Computing device 500 may further include a network interface device 508 which may communicate with a network 520. The computing device 500 also may include a video display unit 510 (e.g., a liquid crystal display (LCD) or a cathode ray tube (CRT)), an alphanumeric input device 512 (e.g., a keyboard), a cursor control device 514 (e.g., a mouse) and an acoustic signal generation device 516 (e.g., a speaker). In one embodiment, video display unit 510, alphanumeric input device 512, and cursor control device 514 may be combined into a single component or device (e.g., an LCD touch screen).

Data storage device 518 may include a computer-readable storage medium 528 on which may be stored one or more sets of instructions that may include perspective selection instructions 525 for carrying out the operations described herein, in accordance with one or more aspects of the present disclosure. The instructions may also reside, completely or at least partially, within main memory 504 and/or within processing device 502 during execution thereof by computing device 500, main memory 504 and processing device 502 also constituting computer-readable media. The instructions may further be transmitted or received over a network 520 via network interface device 508.

While computer-readable storage medium 528 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Reference throughout this specification to "one embodiment" or "an embodiment" means that a particular feature, structure, or characteristic described in connection with the embodiments included in at least one embodiment. Thus, the appearances of the phrase "in one embodiment" or "in an embodiment" in various places throughout this specification are not necessarily all referring to the same embodiment.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

What is claimed is:

1. An apparatus, comprising:
    an imaging system; and
    a processing device, operatively coupled to the imaging system, to:
        identify an image of a region of interest (ROI) from a first perspective, the image having an uncertainty value associated with the ROI;
        generate a model comprising one or more parameters associated with the ROI based on the image;
        determine, using the model, a plurality of tracking quality metrics for a plurality of perspectives that a subsequent image may be captured from by the imaging system of the ROI, the plurality of tracking quality metrics indicating a reduction of the uncertainty value associated with the ROI by the subsequent image; and
        select a second perspective of the plurality of perspectives for the subsequent image based on a corresponding tracking quality metric of the plurality of tracking quality metrics for the second perspective indicating a reduction of the uncertainty value.

2. The apparatus of claim 1, wherein the apparatus comprises a radiation delivery system.

3. The apparatus of claim 2, wherein the second perspective is selected automatically by the processing device during a treatment session by the radiation delivery system.

4. The apparatus of claim 1, wherein the imaging system comprises an X-ray imaging system.

5. The apparatus of claim 1, wherein the imaging system comprises a magnetic resonance (MR) imaging system.

6. The apparatus of claim 1, wherein the processing device is further to:
    cause an imaging source to capture the subsequent image of the ROI from the second perspective;
    receive the subsequent image from the imaging source; and
    update the model based on the subsequent image.

7. The apparatus of claim 1, wherein the imaging system is operatively coupled to a ring gantry and wherein the first perspective corresponds to a first angle of the imaging system relative to the ROI and the second perspective corresponds to a second angle of the imaging system relative to the ROI.

8. The apparatus of claim 1, wherein the model comprises a respiratory motion trajectory associated with the ROI.

9. The apparatus of claim 1, wherein the one or more parameters comprise one or more radiation sensitive structures within the ROI.

10. The apparatus of claim 1, wherein the one or more parameters comprise a visibility of the ROI.

11. A method comprising:
identifying an image of a region of interest (ROI) from a first perspective, the image having an uncertainty value associated with the ROI;
generating a model comprising one or more parameters associated with the ROI based on the image;
determining, using the model, a plurality of tracking quality metrics for a plurality of perspectives that a subsequent image may be captured from by an imaging system of the ROI, the plurality of tracking quality metrics indicating a reduction of the uncertainty value associated with the ROI by the subsequent image; and
selecting, by a processing device, a second perspective of the plurality of perspectives for the subsequent image based on a corresponding tracking quality metric of the plurality of tracking quality metrics for the second perspective indicating a reduction of the uncertainty value.

12. The method of claim 11, wherein the subsequent image is to be captured by the imaging system of a radiation delivery system.

13. The method of claim 12, wherein the second perspective is selected automatically by the processing device during a treatment session by the radiation delivery system.

14. The method of claim 11, wherein the imaging system comprises an X-ray imaging system.

15. The method of claim 11, wherein the imaging system comprises a magnetic resonance (MR) imaging system.

16. The method of claim 11, further comprising:
causing the imaging system to capture the subsequent image of the ROI from the second perspective;
receiving the subsequent image from the imaging system; and
updating the model based on the subsequent image.

17. The method of claim 11, wherein the imaging system is operatively coupled to a ring gantry and wherein the first perspective corresponds to a first angle of the imaging system relative to the ROI and the second perspective corresponds to a second angle of the imaging system relative to the ROI.

18. The method of claim 11, wherein the model comprises a respiratory motion trajectory associated with the ROI.

19. The method of claim 11, wherein the one or more parameters comprise one or more radiation sensitive structures within the ROI.

20. The method of claim 11, wherein the one or more parameters comprise a visibility of the ROI.

21. A non-transitory computer-readable storage medium including instructions that, when executed by a processing device, cause the processing device to:
identify an image of a region of interest (ROI) from a first perspective, the image having an uncertainty value associated with the ROI;
generate a model comprising one or more parameters associated with the ROI based on the image;
determine, using the model, a plurality of tracking quality metrics for a plurality of perspectives that a subsequent image may be captured from by an imaging system of the ROI, the plurality of tracking quality metrics indicating a reduction of the uncertainty value associated with the ROI by the subsequent image; and
select, by the processing device, a second perspective of the plurality of perspectives for the subsequent image based on a corresponding tracking quality metric of the plurality of tracking quality metrics for the second perspective indicating a reduction of the uncertainty value.

22. The non-transitory computer-readable storage medium of claim 21, wherein the subsequent image is to be captured by the imaging system of a radiation delivery system.

23. The non-transitory computer-readable storage medium of claim 22, wherein the second perspective is selected automatically by the processing device during a treatment session by the radiation delivery system.

24. The non-transitory computer-readable storage medium of claim 21, wherein the imaging system comprises an X-ray imaging system.

* * * * *